United States Patent
Sur et al.

(10) Patent No.: US 9,864,947 B1
(45) Date of Patent: Jan. 9, 2018

(54) NEAR FIELD COMMUNICATION FOR A TOBACCO-BASED ARTICLE OR PACKAGE THEREFOR

(71) Applicant: RAI Strategic Holdings, Inc., Winston-Salem, NC (US)

(72) Inventors: Rajesh Sur, Winston-Salem, NC (US); Eric T. Hunt, Pfafftown, NC (US); Stephen B. Sears, Siler City, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

(21) Appl. No.: 15/352,199

(22) Filed: Nov. 15, 2016

(51) Int. Cl.
| G06K 19/06 | (2006.01) |
| G06K 19/077 | (2006.01) |
| A24F 47/00 | (2006.01) |
| A61M 15/06 | (2006.01) |

(52) U.S. Cl.
CPC ...... *G06K 19/07788* (2013.01); *A24F 47/008* (2013.01); *A61M 15/06* (2013.01); *G06K 19/07756* (2013.01); *A61M 2205/50* (2013.01)

(58) Field of Classification Search
CPC .......... A61M 15/06; A61M 2205/6054; A61M 2205/273; A61M 2205/50; G06K 19/0723; G06K 19/077; G06K 19/07788; A24B 15/167; A24D 3/061; F21S 9/02; A24F 47/008
USPC .......................................................... 235/492
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |

(Continued)

FOREIGN PATENT DOCUMENTS

| AU | 276250 | 7/1965 |
| CA | 2 641 869 | 5/2010 |

(Continued)

OTHER PUBLICATIONS

Lehtonen, et al., "From Identification to Authentication—A Review of RFID Product Authentication Techniques", Information Management, pp. 1-17, Apr. 2008.

(Continued)

*Primary Examiner* — Claude J Brown
(74) *Attorney, Agent, or Firm* — Womble Bond Dickinson (US) LLP

(57) ABSTRACT

An apparatus embodied as a tobacco-based article including a consumable material that is tobacco, or that is made, derived from or incorporates tobacco, or as a package for one or more of the tobacco-based article or the consumable material, includes a housing and near field communication (NFC) tag. The housing is structured to retain the tobacco-based article or the consumable material. The NFC tag is configured to store or generate information related to the article or the material. The NFC tag is coupleable with a NFC reader to enable wireless transfer of the information to a computing device to enable authentication of the apparatus, or display or storage of the information, at the computing device or a service platform in communication with the computing device.

19 Claims, 3 Drawing Sheets

(56) References Cited

U.S. PATENT DOCUMENTS

| | | | |
|---|---|---|---|
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 2002/0146242 A1 | 10/2002 | Vieira |
| 2003/0059050 A1* | 3/2003 | Hohberger ............ B41J 17/36 380/270 |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0093448 A1* | 4/2008 | de la Huerga ...... G06F 19/3462 235/385 |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Han |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0006900 A1* | 1/2011 | Nyffeler ................ G06K 19/14 340/572.1 |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0174914 A1* | 7/2012 | Pirshafiey ............ A61M 11/041 128/200.14 |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0197974 A1* | 8/2013 | Romanko ............ G06Q 30/06 705/7.33 |
| 2013/0255702 A1 | 10/2013 | Griffith, Jr. et al. |
| 2013/0282172 A1* | 10/2013 | Chen .................... A47K 5/1217 700/237 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |

(56) References Cited

U.S. PATENT DOCUMENTS

| | | | |
|---|---|---|---|
| 2014/0157583 A1 | 6/2014 | Ward et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2014/0345631 A1 | 11/2014 | Bowen et al. | |
| 2015/0007838 A1 | 1/2015 | Fernando et al. | |
| 2015/0053217 A1 | 2/2015 | Steingraber et al. | |
| 2015/0136158 A1* | 5/2015 | Stevens | A24F 47/008 131/329 |
| 2015/0208731 A1* | 7/2015 | Malamud | H05B 1/0244 131/328 |
| 2015/0238673 A1* | 8/2015 | Gerber | A61M 1/14 210/85 |
| 2015/0245654 A1* | 9/2015 | Memari | A24F 15/12 141/2 |
| 2016/0037826 A1 | 2/2016 | Hearn et al. | |
| 2016/0089508 A1* | 3/2016 | Smith | A61M 15/06 128/200.16 |
| 2016/0114104 A1* | 4/2016 | Hyde | A61M 5/16804 604/890.1 |
| 2017/0014582 A1* | 1/2017 | Skoda | A61M 11/042 |
| 2017/0042246 A1* | 2/2017 | Lau | B65D 25/04 |
| 2017/0064997 A1* | 3/2017 | Murison | A24F 15/12 |
| 2017/0071255 A1* | 3/2017 | Revell | A24F 47/008 |
| 2017/0197777 A1 | 7/2017 | Slooff | |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 97/48293 | 12/1997 |
| WO | WO 03/034847 | 5/2003 |
| WO | WO 2004/043175 | 5/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

OTHER PUBLICATIONS

"About near Field Communication", Ubitap NFC Technologies, pp. 1-5, Retrieved on Oct. 11, 2016.

* cited by examiner

NEAR FIELD COMMUNICATION FOR A TOBACCO-BASED ARTICLE OR PACKAGE THEREFOR

TECHNOLOGICAL FIELD

The present disclosure relates to tobacco-based articles such as cigarettes, cigars, pipes, smokeless tobacco products or aerosol delivery devices, and more particularly to tobacco-based articles or packages for tobacco-based articles equipped with near field communication (NFC) for wireless transfer of information related thereto.

BACKGROUND

Popular tobacco-based articles, such as cigarettes, cigars, pipes, smokeless tobacco products, conventionally have been sold in packages. For cigarettes in particular, each full package typically contains about 20 cigarettes. Cigarettes have been packaged in containers known as so-called "soft packs." See, for example, U.S. Pat. No. 3,695,422 to Tripodi, U.S. Pat. No. 4,717,017 to Sprinkel, Jr., et al., and U.S. Pat. No. 5,333,729 to Wolfe, all of which are incorporated herein by reference. Cigarettes also have been packaged in containers known as so-called "hard packs" or "crush proof boxes." See, for example, U.S. Pat. No. 3,874,581 to Fox et al., U.S. Pat. No. 3,944,066 to Niepmann, and U.S. Pat. No. 4,852,734 to Allen et al., all of which are incorporated herein by reference.

Smokeless tobacco is tobacco that is placed in the mouth and not combusted. There are various types of smokeless tobacco including chewing tobacco, moist smokeless tobacco, snus and dry snuff. Smokeless tobacco products have been packaged in tins, "pucks" or "pots" that are manufactured from metal or plastic. See, for example, U.S. Pat. No. 4,098,421 to Foster, U.S. Pat. No. 4,190,170 to Boyd, U.S. Pat. No. 8,556,070 to Bried et al., U.S. Pat. No. 8,910,781 to Pipes et al., and U.S. Pat. App. Pub. No. 2010/0065076 to Bergstrom et al., U.S. Pat. App. Pub. No. 2010/0065077 to Lofgreen-Ohrn et al., U.S. Pat. App. Pub. No. 2011/0303511 to Brinkley et al., and U.S. Pat. App. Pub. No. 2016/0270440 to Patel et al., all of which are incorporated herein by reference.

In recent years, devices have been proposed as improvements upon, or alternatives to, smoking products that require combusting tobacco for use. Many of these devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., and U.S. Pat. App. Pub. No. 2014/0096781 to Sears et al., all of which are incorporated by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

Some embodiments of aerosol delivery devices such as so-called "e-cigarettes" may employ cartridges to store an aerosol precursor useable in conjunction with a control body of an aerosol delivery device to form aerosol and simulate smoking, as described above. The cartridge and control body may be packaged separately or together, and separately-packaged replacements for each may be offered.

In addition to providing means for distributing, storing or otherwise containing one or more tobacco-based articles, their packages may be utilized to communicate information to a consumer. For instance, graphics and text are typically applied to the exterior of the package to communicate various information regarding the articles, including branding, advertising, regulatory information, nutritional information, and promotional information. Conventional packages are often relatively small in size and may have a limited visible exterior surface area for providing information. Thus, the information that may be provided via the available display surfaces may also be limited.

It may therefore be desirable to provide tobacco-based articles and their packaging with additional or alternative means to transfer information related thereto.

BRIEF SUMMARY

The present disclosure relates to tobacco-based articles such as cigarettes, cigars, pipes, smokeless tobacco products, aerosol delivery devices and the like, packages for smoking articles, tobacco or tobacco-based, consumable material, methods of forming such articles and packages, and elements of such articles and packages. The present disclosure includes, without limitation, the following example implementations.

Some example implementations provide an apparatus embodied as a tobacco-based article including a material that is tobacco, or that is made, derived from or incorporates tobacco, or as a package for one or more of the tobacco-based article or the material, the apparatus comprising a housing structured to retain the tobacco-based article or the material; and on or within the housing, a near field communication (NFC) tag configured to wirelessly communicate with a computing device equipped with a NFC reader, the NFC tag comprising: an antenna; and an integrated circuit (IC) configured to store or generate information including at least an authentication indicia that enables authentication of the apparatus, a manufacture date of the apparatus, content regarding the apparatus or the material, or a web address to a web resource with the content, or a geographic location of an intended distributer or retailer of the apparatus, wherein the antenna is coupleable with a corresponding antenna of the NFC reader to enable wireless transfer of the information to the computing device to enable authentication of the apparatus, or display or storage of the manufacture date, the content or the geographic location, at the computing device or a service platform in communication with the computing device.

In some example implementations of the apparatus of the preceding or any subsequent example implementation, or any combination thereof, the apparatus is embodied as an aerosol delivery device, a control body or a cartridge for the aerosol delivery device, or a package for one or more of the aerosol delivery device, the control body or the cartridge, wherein the consumable material is an aerosol precursor composition comprising nicotine.

In some example implementations of the apparatus of any preceding or any subsequent example implementation, or any combination thereof, the apparatus is embodied as a package for one or more of the tobacco-based article in which the tobacco-based article is embodied as a cigarette, cigar, pipe or smokeless tobacco product.

In some example implementations of the apparatus of the preceding or any subsequent example implementation, or any combination thereof, the IC being configured to store or generate the information includes being configured to store or generate at least the authentication indicia, and the antenna is coupleable with the corresponding antenna of the NFC reader to enable wireless transfer of the information to the computing device to enable the authentication of the apparatus based on the authentication indicia.

In some example implementations of the apparatus of the preceding or any subsequent example implementation, or any combination thereof, the IC being configured to store or generate the information includes being configured to store or generate at least the manufacture date, and the antenna is coupleable with the corresponding antenna of the NFC reader to enable wireless transfer of the information to the computing device to enable the display or storage of the manufacture date.

In some example implementations of the apparatus of the preceding or any subsequent example implementation, or any combination thereof, the IC being configured to store or generate the information includes being configured to store or generate at least the content or the web address to the web resource with the content, and the antenna is coupleable with the corresponding antenna of the NFC reader to enable wireless transfer of the information to the computing device to enable the display or storage of the content.

In some example implementations of the apparatus of the preceding or any subsequent example implementation, or any combination thereof, the content includes a description of the apparatus or the consumable material, or a coupon redeemable for a discount or rebate for the apparatus or another product.

In some example implementations of the apparatus of the preceding or any subsequent example implementation, or any combination thereof, the content includes a list of retailers that are authorized to sell the apparatus.

In some example implementations of the apparatus of the preceding or any subsequent example implementation, or any combination thereof, the content includes a suggested food or drink accompaniment for the consumable material.

In some example implementations of the apparatus of the preceding or any subsequent example implementation, or any combination thereof, the IC being configured to store or generate the information includes being configured to store or generate at least the geographic location, and the antenna is coupleable with the corresponding antenna of the NFC reader to enable wireless transfer of the information to the computing device to enable the display or storage of the geographic location.

Some example implementations provide a cartridge coupled or coupleable with a control body that is equipped with a control component, the control body being coupled or coupleable with the cartridge to form an aerosol delivery device, the cartridge comprising at least one housing enclosing a reservoir configured to retain an aerosol precursor composition; a heating element controllable to activate and vaporize components of the aerosol precursor composition; and a near field communication (NFC) tag configured to wirelessly communicate with a computing device equipped with a NFC reader, the NFC tag comprising: an antenna; and an integrated circuit (IC) configured to store or generate information including at least an authentication indicia that enables authentication of the cartridge, a manufacture date of the cartridge, content regarding the cartridge or the aerosol precursor composition, or a web address to a web resource with the content, or a geographic location of an intended distributer or retailer of the cartridge, wherein the antenna is coupleable with a corresponding antenna of the NFC reader to enable wireless transfer of the information to the computing device to enable authentication of the cartridge, or display or storage of the manufacture date, the content or the geographic location, at the computing device or a service platform in communication with the computing device.

In some example implementations of the cartridge of the preceding or any subsequent example implementation, or any combination thereof, the aerosol precursor composition comprises nicotine.

In some example implementations of the cartridge of the preceding or any subsequent example implementation, or any combination thereof, the IC being configured to store or generate the information includes being configured to store or generate at least the authentication indicia, and the antenna is coupleable with the corresponding antenna of the NFC reader to enable wireless transfer of the information to the computing device to enable the authentication of the cartridge based on the authentication indicia.

In some example implementations of the cartridge of the preceding or any subsequent example implementation, or any combination thereof, the computing device is embodied as the control body with which the cartridge is coupled or coupleable to form the aerosol delivery device, and the wireless transfer of the information is to enable authentication of the cartridge and thereby authorization of the cartridge for use with the control body.

In some example implementations of the cartridge of the preceding or any subsequent example implementation, or any combination thereof, the IC being configured to store or generate the information includes being configured to store or generate at least the manufacture date, and the antenna is coupleable with the corresponding antenna of the NFC reader to enable wireless transfer of the information to the computing device to enable the display or storage of the manufacture date.

In some example implementations of the cartridge of the preceding or any subsequent example implementation, or any combination thereof, the IC being configured to store or generate the information includes being configured to store or generate at least the content or the web address to the web resource with the content, and the antenna is coupleable with the corresponding antenna of the NFC reader to enable wireless transfer of the information to the computing device to enable the display or storage of the content.

In some example implementations of the cartridge of the preceding or any subsequent example implementation, or any combination thereof, the content includes a description of the cartridge or the aerosol precursor composition, or a coupon redeemable for a discount or rebate for the cartridge or another product.

In some example implementations of the cartridge of the preceding or any subsequent example implementation, or any combination thereof, the content includes a list of retailers that are authorized to sell the cartridge.

In some example implementations of the cartridge of the preceding or any subsequent example implementation, or any combination thereof, the content includes a suggested food or drink accompaniment for the aerosol precursor composition.

In some example implementations of the cartridge of the preceding or any subsequent example implementation, or any combination thereof, the IC being configured to store or generate the information includes being configured to store or generate at least the geographic location, and the antenna is coupleable with the corresponding antenna of the NFC reader to enable wireless transfer of the information to the computing device to enable the display or storage of the geographic location.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

Figure 1:
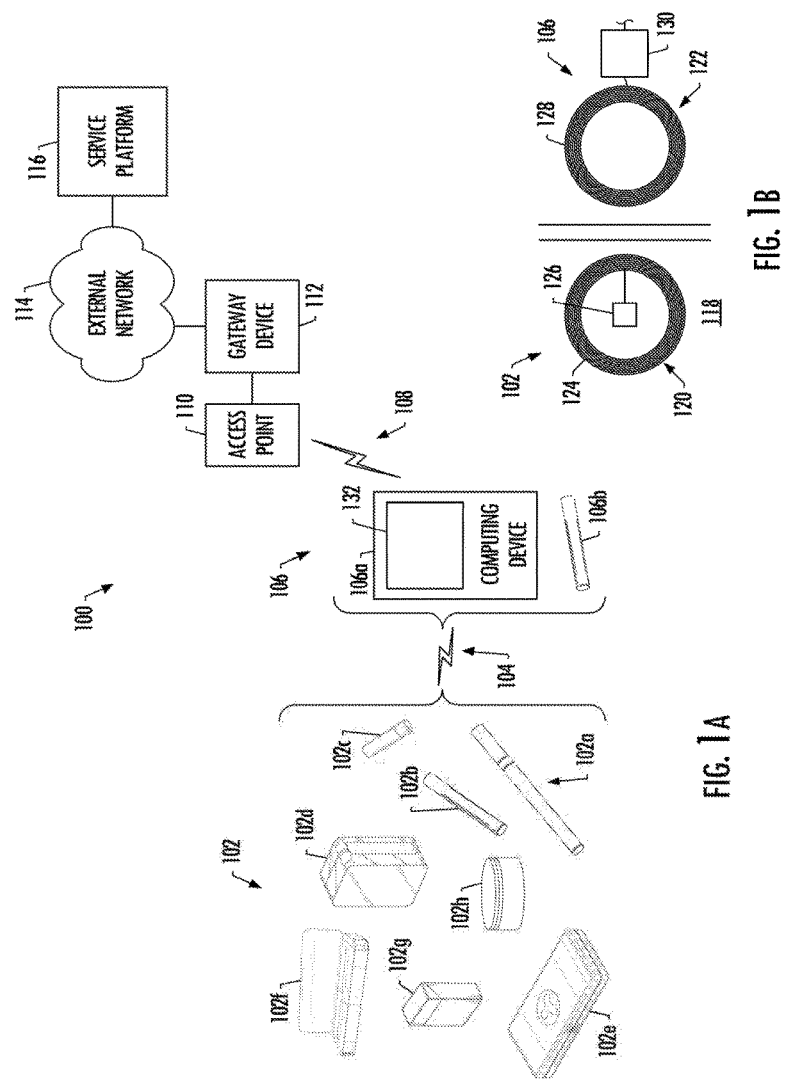
FIGS. 1A and 1B illustrate a system including an apparatus equipped with near field communication (NFC) for wireless communication with a computing device, according to various example implementations of the present disclosure.

Example implementations of the present disclosure are generally directed to a tobacco-based article or package equipped with near field communication (NFC) for wireless communication of information related to the article or its consumable tobacco-based material. FIGS. 1A and 1B in particular illustrate a system 100 including an apparatus 102 embodied as a tobacco-based article including a consumable material that is tobacco, or that is made, derived from or incorporates tobacco, or as a package for one or more of the tobacco-based article or the consumable material.

In some examples, the apparatus is embodied as an aerosol delivery device 102a, a control body 102b or a cartridge 102c for the aerosol delivery device, or a package 102d, 102e, 102f for one or more of the aerosol delivery device, the cartridge or the control body; and in these examples, the consumable material is an aerosol precursor composition comprising nicotine. In other examples, the apparatus is embodied as a package 102g, 102h for one or more of the tobacco-based article in which the tobacco-based article is embodied as a cigarette, cigar, pipe or smokeless tobacco product.

In accordance with example implementations of the present disclosure, the apparatus 102 is capable of NFC communication 104 with a computing device 106. This computing device may also be embodied as a number of different devices, such as any of a number of different mobile computers 106a. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. In yet another example in which the apparatus is embodied as a cartridge 102c for an aerosol delivery device, the computing device is embodied as a control body 106b for the aerosol delivery device.

As described in greater detail below, the aerosol delivery device 102a of example implementations uses electrical energy to heat a material (preferably without combusting the material to any significant degree) to form an inhalable substance; and components of the device such as a control body 102b and cartridge 102c have the form of articles most preferably are sufficiently compact to be considered handheld devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein.

In some example implementations, components of aerosol delivery devices 102a may be characterized as electronic cigarettes, and those electronic cigarettes most preferably incorporate tobacco and/or components derived from tobacco, and hence deliver tobacco derived components in aerosol form. The consumable material in these examples is an aerosol precursor composition, also referred to as a vapor precursor composition, commonly a liquid capable of yielding an aerosol upon application of sufficient heat, such as ingredients commonly referred to as "smoke juice," "e-liquid" and "e-juice." The aerosol precursor composition may comprise a variety of components including, by way of example, a polyhydric alcohol (e.g., glycerin, propylene glycol or a mixture thereof), nicotine, tobacco, tobacco extract and/or flavorants. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference.

The aerosol delivery device 102a, control body 102b, 106b and/or cartridge 102c may be or may be derived from any of a number of commercially-available electronic aerosol delivery devices, which may be equipped for NFC communication 104 as described herein. Further details regarding a suitable aerosol delivery device, cartridge and control body, including examples of commercially-available products, are described in U.S. Pat. App. Pub. No. 2014/0096782 to Ampolini et al., U.S. Pat. App. Pub. No. 2015/0059780 to Davis et al., U.S. patent application Ser. No. 15/222,615 to Watson et al., filed Jul. 28, 2016, and U.S. patent application Ser. No. 15/291,771 to Sur et al., filed Oct. 12, 2016, all of which are incorporated herein by reference.

As with the aerosol delivery device 102a, control body 102b, 106b and/or cartridge 102c, the package 102d, 102e, 102f may be or may be derived from the package in which any of the aforementioned or other commercially-available devices or components are distributed, sold, stored or otherwise contained, in which the package may be equipped for NFC communication 104 as described herein. Likewise, packages 102g, 102h for tobacco-based articles embodied as cigarettes, cigars, pipes or smokeless tobacco products may be or may be derived from the package in which commercially-available tobacco-based articles are distributed, sold, stored or otherwise contained. More particular examples of suitable packages for an aerosol delivery device, cartridge and/or control body are described in U.S. Pat. No. D697,791 to Jones et al., U.S. Pat. No. D709,758 to Burdock-Latter et al., U.S. Pat. No. D715,051 to Tung et al., and U.S. Pat. App. Pub. No. 2016/0075467 to Pipes et al., all of which are incorporated herein by reference. Examples of packages for cigarettes but that may also be suitable for other tobacco-based products are described in U.S. patent application Ser. No. 15/097,019 to Sebastian et al., filed Apr. 12, 2016, which is also incorporated herein by reference. And examples of smokeless tobacco products and packages for smokeless tobacco products are described in U.S. Pat. App. Pub. No. 2013/0206150 to Duggins et al., U.S. Pat. App. Pub. No. 2015/0136618 to Patel et al., U.S. Pat. App. Pub. No. 2015/0274401 to Mabe et al., U.S. Pat. App. Pub. No. 2015/0321787 to Stebbins et al., and U.S. Pat. App. Pub. No. 2016/0157515 to Chapman et al., all of which are incorporated herein by reference.

Returning to the computing device 106, in some examples, the computing device is capable of not only NFC communication 104 with the apparatus 102, but also capable of connection to a wireless local area network (WLAN) 108. Examples of suitable WLAN technologies include those based on or specified by IEEE 802.11 standards and marketed as Wi-Fi. The WLAN includes appropriate networking hardware, some of which may be integral and others of which may be separate and interconnected. As shown, for example, the WLAN includes a wireless access point 110 configured to permit wireless devices including the computing device to connect to the WLAN. As also shown, for example, the WLAN may include a gateway device 112 such as a residential gateway configured to connect the WLAN to an external computer network 114 such as a wide area network (WAN) like the Internet. In some examples, the wireless access point or gateway device may include an integrated router to which other systems or devices may be connected. The WLAN may also include other integral or separate and connected networking hardware, such as a network switch, hub, digital subscriber line (DSL) modem, cable modem or the like.

In some examples, the system 100 further includes a service platform 116, which may be embodied as a computer system accessible by the WLAN 108 or external network 114 (as shown). The service platform may include one or more servers, such as may be provided by one or more web servers, a cloud computing infrastructure or the like. In some examples, the service platform is embodied as a distributed computing apparatus including multiple computing devices, such as may be used to provide a cloud computing infrastructure. And in these examples, the computing devices that form the service platform may be in communication with each other via a network such as the external network.

In some examples, the service platform 116 is accessible by the computing device 106 over the WLAN 108 and external network 114, and configured to provide one or more services related to the apparatus 102 and perhaps others of the apparatus. For example, the service platform may be operated by a manufacturer of a tobacco-based article, a vendor of a tobacco-based article or another entity with interest in the manufacture, distribution or maintenance of an aerosol delivery device. The service platform may enable a user to access and use various features, such as those described below that may be performed at the computing device or the service platform.

The computing device 106 may include or otherwise provide an installed application or other interface through which the service platform 116 may be accessible. This application or other interface may be or may be provided by a thin client and/or other client application, such as a web browser application through which a web page provided by the service platform may be accessible. As another example, the application or other interface may be or may be provided by a dedicated application, such as a mobile app installed on a computing device embodied as a mobile computer 106a.

As shown more particularly in FIG. 1B, in some examples, the apparatus 102 includes a housing 118 structured to retain the tobacco-based article or the consumable material; and on or within the housing, a NFC tag 120 configured to wirelessly communicate with the computing device 106 equipped with a NFC reader 122. The NFC tag includes an antenna 124 and an integrated circuit (IC) 126 configured to store or generate information related to the article or the material. Examples of suitable NFC tags include ST25TA series NFC tags from STMicroelectronics, and RF430CC330 and RF430FRL15x tags from Texas Instruments. Examples of suitable NFC readers for high-frequency (HF) include AS3909, AS3910, AS3911B, AS3914 and AS3915 from ams AG, and for ultra-high frequency (UHF) include AS3980, AS3991, AS3992, AS3993 from ams AG. Another example of a suitable NFC reader is the TRF79xx reader from Texas Instruments.

The antenna 124 of the NFC tag 120 is coupleable with a corresponding antenna 128 of the NFC reader 122 to enable wireless transfer of the information to the computing device 106. As shown, the NFC reader may also include appropriate circuitry 130 such as a microprocessor, individually or as part of a microcontroller, a microcontroller unit (MCU), or the like. In some examples, the information stored by the IC 126 includes at least an authentication indicia that enables authentication of the apparatus, a manufacture date of the apparatus, content regarding the apparatus or the consumable material, or a web address to a web resource with the content, or a geographic location of an intended distributer or retailer of the apparatus. The information may be stored or generated in cleartext, or the information may be encrypted and thereby access restricted. According to example implementations, then, the wireless transfer of information to the computing device enables authentication of the apparatus 102, or display or storage of the manufacture date, the content or the geographic location, at the computing device or the service platform 116 in communication with the computing device. In some examples, the computing device includes a display device 132 for display of the manufacture date, the content or the geographic location.

In some in which the information includes at least the authentication indicia, the antenna 124 is coupleable with the corresponding antenna 128 of the NFC reader 122 to enable wireless transfer of the information to the computing device to enable the authentication of the apparatus 102 based on the authentication indicia. Examples of suitable authentication indicia include a unique serial number or other identifier (ID) of the apparatus, an access key, digital signature or other code, or the like. In another example, the authentication indicia may indicate a manufacturer of the apparatus.

In these examples, the computing device 106 or service platform 116 may be configured to authenticate the apparatus 102. This authentication may involve, for example, a determination as to whether an aerosol delivery device 102*a*, a control body 102*b* or a cartridge 102*c* for the aerosol delivery device, a package 102*d*, 102*e*, 102*f* for one or more of the aerosol delivery device, the cartridge or the control body, or a package 102*g*, 102*h* for one or more of a cigarette, cigar, pipe or smokeless tobacco product is authentic or counterfeit.

As explained in greater detail below, in other examples in which the apparatus and computing device are embodied as respectively a cartridge 102*c* and a control body 106*b* of an aerosol delivery device, the control body may be configured to authenticate the cartridge to determine whether the cartridge is authorized for use with the control body. This authentication may involve, for example, a determination as to whether manufacturer of the cartridge is the same as or authorized by the manufacturer of the control body, and thereby authorized for use with the control body (i.e., the cartridge may only be used with the control body if the cartridge is manufactured or authorized by the manufacturer of the control body).

In some examples, authentication of the apparatus 102 may involve a challenge-response authentication in which the apparatus is prompted to provide a response to a challenge wirelessly transferred from the computing device 106 to the apparatus. In these and other examples, the apparatus may be equipped with a suitable authentication device integrated with or coupled to the IC 126. Examples of suitable authentication devices include the bq26150 authentication device from Texas Instruments, the ATSHA204 and ATSHA204A authentication devices from Atmel Corporation, and the like. Further details of authentication processes suitable for example implementations of the present disclosure are described in U.S. Pat. App. Pub. No. 2014/0096782 to Ampolini et al., which is incorporated by reference.

In some examples in which the information includes at least the manufacture date, the antenna 124 is coupleable with the corresponding antenna 128 of the NFC reader 122 to enable wireless transfer of the information to the computing device 106 to enable the display or storage of the manufacture date. The manufacture date may provide an indication of an age or freshness of the consumable material of the apparatus 102, which again, may be tobacco, or made, derived from or incorporate tobacco.

In some examples in which the information includes at least the content or the web address to the web resource with the content, the antenna 124 is coupleable with the corresponding antenna 128 of the NFC reader 122 to enable wireless transfer of the information to the computing device 106 to enable the display or storage of the content. The web address may be a uniform resource identifier (URI) such as a uniform resource locator (URL), an Internationalized Resource Identifier (IRI), or any other string of characters from which the web resource may be identified. Examples of suitable web resources electronic documents (e.g., web pages, websites), images, services or collections of other resources. In accordance with some examples, the content of the web resource includes one or more of a description of the apparatus 102 or the consumable material, a coupon redeemable for a discount or rebate for the apparatus or another product, a list of retailers that are authorized to sell the apparatus, or a suggested food or drink accompaniment for the consumable material.

In yet another example, the content includes the geographic location of an intended distributer or retailer of the apparatus 102, which may or may not be accompanied by the name of the intended distributer or retailer. Although described as content of a web resource identified by a web address generated or stored by the IC 126, the IC may be configured to directly store or generate the content itself. In the context of the geographic location of an intended distributer or retailer, in some examples, the antenna 124 is coupleable with the corresponding antenna 128 of the NFC reader 122 to enable wireless transfer of the information to the computing device 106 to enable the display or storage of the geographic location. The geographic location may be in any of a number of different formats. In some examples, the geographic location is in the format of geographic coordinates. Additionally or alternatively, in some examples, the geographic location is in the format of a partial or complete address, such as one or more of a street, city area/district, city/town/village, county, postal code or country. In these examples, the geographic location may be displayed textually and/or graphically such as on a geographic map of or including the geographic location.

Figure 2:
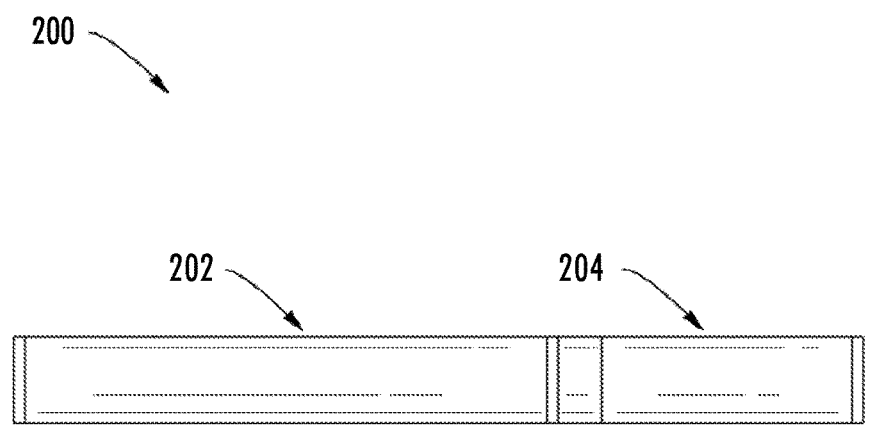
FIG. 2 illustrates a side view of an aerosol delivery device including a cartridge coupled to a control body, according to an example implementation of the present disclosure.
Figure 3:
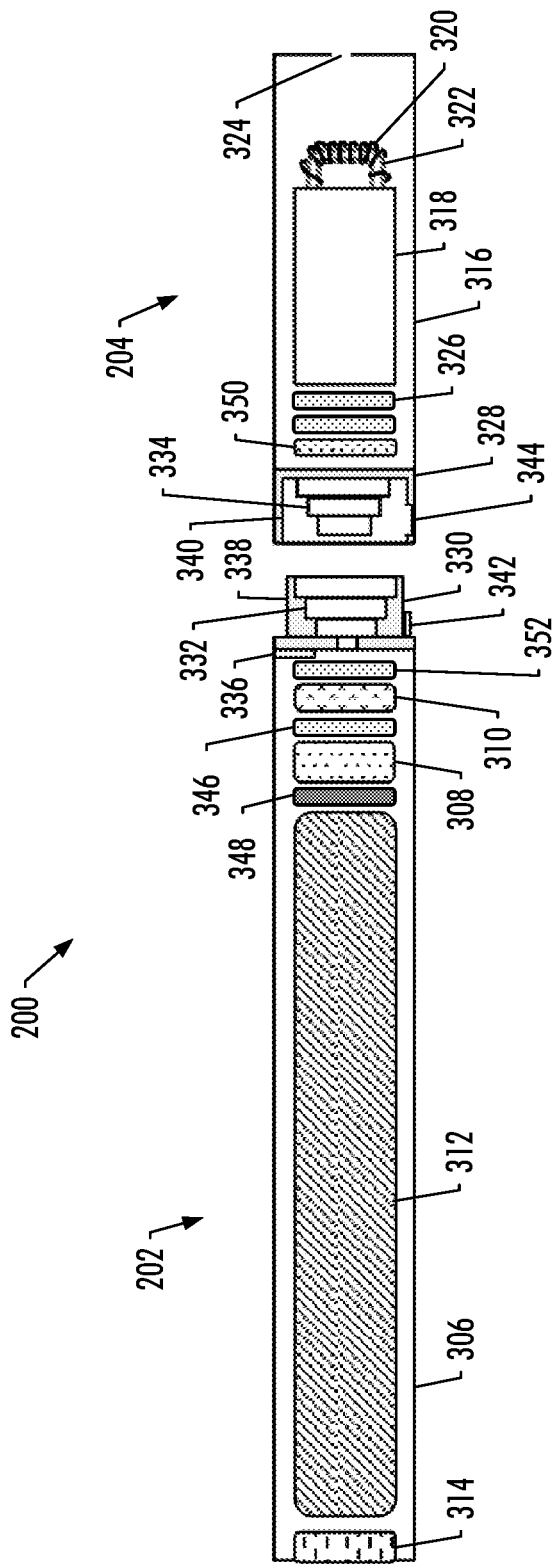
FIG. 3 is a partially cut-away view of the aerosol delivery device according to various example implementations.

To further illustrate example implementations of the present disclosure, further detail regarding the aerosol delivery device 102*a*, and the control body 102*b*, 106*b* and cartridge 102*c* follows with reference to FIGS. 2 and 3. Even further detail regarding suitable variations in the aerosol delivery device, control body and cartridge may be found in the previously-cited and incorporated U.S. patent application Ser. No. 15/291,771 to Sur et al., filed Oct. 12, 2016.

More particularly, FIGS. 2 and 3 illustrate respectively a side view and a partially cut-away view of an aerosol delivery device 200 including a control body 202 and a cartridge 204, which in some example implementations may correspond to one or more of respectively the aerosol delivery device 102*a*, control body 102*b*, 106*b* or cartridge 102*c*. In some examples, the control body 202 is equipped and capable of corresponding to both the control body 102*b* and 106*b*.

FIG. 2 illustrates the control body 202 and the cartridge 204 coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device 200 may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 202 or the cartridge 204 of the aerosol delivery device 200 may be referred to as being disposable or as being reusable. For example, the control body may have a replaceable battery, or a rechargeable battery, supercapacitor or solid state battery, and thus may be combined with any type of recharging technology, including connection to a typical wall outlet, connection to a car charger (i.e., a cigarette lighter receptacle), connection to a computer, such as through a universal serial bus (USB) cable or connector, connection to a photovoltaic cell, gallium arsenide (GaAs) photovoltaic cell or the like (sometimes referred to as a solar cell) or solar panel of solar cells, or connection to a RF-to-DC converter. Further, in some example implementations, the cartridge may comprise a single-use cartridge, as disclosed in U.S. Pat. No. 8,910,639 to Chang et al., which is incorporated herein by reference.

FIG. 3 more particularly illustrates the aerosol delivery device 200, in accordance with some example implementations. As seen in the cut-away view illustrated therein, again, the aerosol delivery device can comprise a control body 202 and a cartridge 204 each of which include a number of respective components. The components illustrated in FIG. 3 are representative of the components that may be present in a control body and cartridge and are not intended to limit the scope of components that are encompassed by the present disclosure. As shown, for example, the control body can be formed of a control body shell 306 that can include a control component 308 (e.g., a microprocessor, individually or as part of a microcontroller), a flow sensor 310, a power source 312 and one or more light-emitting diodes (LEDs) 314, and such components can be variably aligned. The power source may include, for example, a battery (single-use or rechargeable), lithium-ion battery (LiB), solid-state battery (SSB), rechargeable thin-film SSB, rechargeable supercapacitor or the like, or some combination thereof. Some examples of a suitable power source are provided in U.S. patent application Ser. No. 14/918,926 to Sur et al., filed Oct. 21, 2015, which is incorporated herein by reference. The LED may be one example of a suitable visual indicator with which the aerosol delivery device may be equipped. Other indicators such as audio indicators (e.g., speakers), haptic indicators (e.g., vibration motors) or the like can be included in addition to or as an alternative to visual indicators such as the LED, quantum dot enabled LEDs, multiple RGB LEDs.

The cartridge 204 can be formed of a cartridge shell 316 enclosing a reservoir 318 configured to retain the aerosol precursor composition, and including a heater 322 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater. And in some examples, the shell may correspond to the housing 118 shown and described above with respect to FIG. 1B.

As shown in FIG. 3, in some examples, the reservoir 318 may be in fluid communication with a liquid transport element 320 adapted to wick or otherwise transport an aerosol precursor composition stored in the reservoir housing to the heater 322. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 322. The heater in these examples may be a resistive heating element such as a wire coil, micro heater or the like. Example materials from which the heating element may be formed include Kanthal (Fe-CrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 3 as described herein.

An opening 324 may be present in the cartridge shell 316 (e.g., at the mouthend) to allow for egress of formed aerosol from the cartridge 204.

The cartridge 204 also may include one or more electronic components 326, which may include an integrated circuit, a memory component (e.g., EEPROM, flash memory), a sensor, or the like. The electronic components may be adapted to communicate with the control component 308 and/or with an external device by wired or wireless means. The electronic components may be positioned anywhere within the cartridge or a base 328 thereof.

Although the control component 308 and the flow sensor 310 are illustrated separately, it is understood that various electronic components including the control component and the flow sensor may be combined on an electronic printed circuit board (PCB) that supports and electrically connects the electronic components. Further, the PCB may be positioned horizontally relative the illustration of FIG. 1 in that the PCB can be lengthwise parallel to the central axis of the control body. In some examples, the air flow sensor may comprise its own PCB or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 202 and the cartridge 204 may include components adapted to facilitate a fluid engagement therebetween. As illustrated in FIG. 3, the control body can include a coupler 330 having a cavity 332 therein. The base 328 of the cartridge can be adapted to engage the coupler and can include a projection 334 adapted to fit within the cavity. Such engagement can facilitate a stable connection between the control body and the cartridge as well as establish an electrical connection between the power source 312 and control component 308 in the control body and the heater 322 in the cartridge. Further, the control body shell 306 can include an air intake 336, which may be a notch in the shell where it connects to the coupler that allows for passage of ambient air around the coupler and into the shell where it then passes through the cavity 332 of the coupler and into the cartridge through the projection 334.

A coupler and a base useful according to the present disclosure are described in U.S. Pat. App. Pub. No. 2014/0261495 to Novak et al., which is incorporated herein by reference. For example, the coupler 330 as seen in FIG. 3 may define an outer periphery 338 configured to mate with an inner periphery 340 of the base 328. In one example the inner periphery of the base may define a radius that is substantially equal to, or slightly greater than, a radius of the outer periphery of the coupler. Further, the coupler may define one or more protrusions 342 at the outer periphery configured to engage one or more recesses 344 defined at the inner periphery of the base. However, various other examples of structures, shapes and components may be employed to couple the base to the coupler. In some examples the connection between the base of the cartridge 204 and the coupler of the control body 202 may be substantially permanent, whereas in other examples the connection therebetween may be releasable such that, for example, the control body may be reused with one or more additional cartridges that may be disposable and/or refillable.

The aerosol delivery device 200 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 318 illustrated in FIG. 3 can be a container or can be a fibrous reservoir, as presently described. For example, the reservoir can comprise one or more layers of nonwoven fibers substantially formed into the shape of a tube encircling the interior of the cartridge shell 316, in this example. An aerosol precursor composition can be retained in the reservoir. Liquid components, for example, can be sorptively retained by the reservoir. The reservoir can be in fluid connection with the liquid transport element 320. The liquid transport element can transport the aerosol precursor composition stored in the reservoir via capillary action to the heater 322 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 3 as described herein. In particular, specific combinations of heating members and transport elements as further described below may be incorporated into devices such as illustrated in FIG. 3 as described herein.

In use, when a user draws on the aerosol delivery device 200, airflow is detected by the flow sensor 310, and the heater 322 is activated to vaporize components of the aerosol precursor composition. Drawing upon the mouthend of the aerosol delivery device causes ambient air to enter the air intake 336 and pass through the cavity 332 in the coupler 330 and the central opening in the projection 334 of the base 328. In the cartridge 204, the drawn air combines with the formed vapor to form an aerosol. The aerosol is whisked, aspirated or otherwise drawn away from the heater and out the opening 324 in the mouthend of the aerosol delivery device.

The aerosol delivery device 200 most preferably incorporates the control component 308 or another control mechanism for controlling the amount of electric power to the heater 322 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. Pat. App. Pub. No. 2015/0257445 to Henry et al., all of which are incorporated herein by reference.

As indicated above, the control component 308 includes a number of electronic components, and in some examples may be formed of a PCB. The electronic components may include a microprocessor or processor core, and a memory. In some examples, the control component may include a microcontroller with integrated processor core and memory, and may further include one or more integrated input/output peripherals. In some examples, the control component may be coupled to a communication interface 346 to enable wireless communication with one or more networks, computing devices or other appropriately-enabled devices. Examples of suitable communication interfaces are disclosed in U.S. patent application Ser. No. 14/638,562 to Marion et al., filed Mar. 4, 2015, the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

In examples in which the aerosol delivery device 200, control body 202 or cartridge 204 correspond to respectively the aerosol delivery device 102a, control body 102b or cartridge 102c, either or both the control body and cartridge is further equipped with or otherwise have a NFC tag 348, 350. The NFC tag 248, 350 corresponds to the NFC tag 120 shown in FIG. 1B and thereby includes its antenna 124, and its IC 126 configured to store or generate information related to the article or the material. In these examples, the aerosol delivery device 200, control body 202 or cartridge 204, and the NFC tag 348, 350, are configured to operate as described above with respect to FIGS. 1A and 1B.

In examples in which the control body 202 and cartridge 204 correspond to respectively the control body 106b and cartridge 102c, while the cartridge is equipped with the NFC tag 350, the control body is further equipped with a NFC reader 352. The NFC reader 352 corresponds to the NFC reader 122 shown in FIG. 1B and thereby includes its corresponding antenna 128 and circuitry 130. In these examples, the control body 202 and cartridge 204, and the NFC tag 350 and NFC reader 352, are configured to operate as described above with respect to FIGS. 1A and 1B.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an apparatus according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus embodied as a tobacco-based article including a consumable material that is tobacco, or that is made, derived from or incorporates tobacco, or as a package for one or more of the tobacco-based article or the consumable material, the apparatus comprising:
    a housing structured to retain the tobacco-based article or the consumable material; and on or within the housing,
    a near field communication (NFC) tag configured to wirelessly communicate with a computing device equipped with a NFC reader, the NFC tag comprising:
        an antenna; and
        an integrated circuit (IC) configured to store or generate information including at least a geographic location of an intended distributer or retailer of the apparatus,
        wherein the antenna is coupleable with a corresponding antenna of the NFC reader to enable wireless transfer of the information to the computing device to enable display or storage of the geographic location, the display or storage being at the computing device or a service platform in communication with the computing device.

2. The apparatus of claim 1 embodied as an aerosol delivery device, a control body or a cartridge for the aerosol delivery device, or a package for one or more of the aerosol delivery device, the control body or the cartridge, wherein the consumable material is an aerosol precursor composition comprising nicotine.

3. The apparatus of claim 1 embodied as a package for one or more of the tobacco-based article in which the tobacco-based article is embodied as a cigarette, cigar, pipe or smokeless tobacco product.

4. The apparatus of claim 1, wherein the IC being configured to store or generate the information includes being configured to store or generate the information further including an authentication indicia that enables authentication of the apparatus, and the antenna is coupleable with the corresponding antenna of the NFC reader to enable wireless transfer of the information to the computing device to enable authentication of the apparatus based on the authentication indicia.

5. The apparatus of claim 1, wherein the IC being configured to store or generate the information includes being configured to store or generate the information further including a manufacture date of the apparatus, and the antenna is coupleable with the corresponding antenna of the NFC reader to enable wireless transfer of the information to the computing device to enable display or storage of the manufacture date.

6. The apparatus of claim 1, wherein the IC being configured to store or generate the information includes being configured to store or generate the information further including content regarding the apparatus or the consumable material, or a web address to a web resource with the content, and the antenna is coupleable with the corresponding antenna of the NFC reader to enable wireless transfer of the information to the computing device to enable display or storage of the content.

7. The apparatus of claim 6, wherein the content includes a description of the apparatus or the consumable material, or a coupon redeemable for a discount or rebate for the apparatus or another product.

8. The apparatus of claim 6, wherein the content includes a list of retailers that are authorized to sell the apparatus.

9. The apparatus of claim 6, wherein the content includes a suggested food or drink accompaniment for the consumable material.

10. A cartridge coupled or coupleable with a control body that is equipped with a control component, the control body being coupled or coupleable with the cartridge to form an aerosol delivery device, the cartridge comprising:
    at least one housing enclosing a reservoir configured to retain an aerosol precursor composition;
    a heating element controllable to activate and vaporize components of the aerosol precursor composition; and
    a near field communication (NFC) tag configured to wirelessly communicate with a computing device equipped with a NFC reader, the NFC tag comprising:
        an antenna; and
        an integrated circuit (IC) being configured to store or generate information including at least a geographic location of an intended distributer or retailer of the cartridge,
        wherein the antenna is coupleable with a corresponding antenna of the NFC reader to enable wireless transfer of the information to the computing device to enable display or storage of the geographic location, the display or storage being at the computing device or a service platform in communication with the computing device.

11. The cartridge of claim 10, wherein the aerosol precursor composition comprises nicotine.

12. The cartridge of claim 10, wherein the IC being configured to store or generate the information includes being configured to store or generate the information further including an authentication indicia that enables authentication of the cartridge, and the antenna is coupleable with the corresponding antenna of the NFC reader to enable wireless transfer of the information to the computing device to enable authentication of the cartridge based on the authentication indicia.

13. The cartridge of claim 10, wherein the IC being configured to store or generate the information includes being configured to store or generate the information further including a manufacture date of the cartridge, and the antenna is coupleable with the corresponding antenna of the NFC reader to enable wireless transfer of the information to the computing device to enable display or storage of the manufacture date.

14. The cartridge of claim 10, wherein the IC being configured to store or generate the information includes being configured to store or generate the information further including content regarding the apparatus or the consumable material, or a web address to a web resource with the content, and the antenna is coupleable with the corresponding antenna of the NFC reader to enable wireless transfer of the information to the computing device to enable display or storage of the content.

15. The cartridge of claim 14, wherein the content includes a description of the cartridge or the aerosol precursor composition, or a coupon redeemable for a discount or rebate for the cartridge or another product.

16. The cartridge of claim 14, wherein the content includes a list of retailers that are authorized to sell the cartridge.

17. The cartridge of claim 14, wherein the content includes a suggested food or drink accompaniment for the aerosol precursor composition.

18. A cartridge coupled or coupleable with a control body that is equipped with a control component, the control body being coupled or coupleable with the cartridge to form an aerosol delivery device, the cartridge comprising:

at least one housing enclosing a reservoir configured to retain an aerosol precursor composition;

a heating element controllable to activate and vaporize components of the aerosol precursor composition; and a near field communication (NFC) tag configured to wirelessly communicate with a computing device equipped with a NFC reader, the NFC tag comprising:

an antenna; and an integrated circuit (IC) being configured to store or generate information including at least an authentication indicia that enables authentication of the cartridge, wherein the antenna is coupleable with a corresponding antenna of the NFC reader to enable wireless transfer of the information to the computing device to enable authentication of the cartridge at the computing device, and wherein the computing device is embodied as the control body with which the cartridge is coupled or coupleable to form the aerosol delivery device, and the wireless transfer of the information is to enable authentication of the cartridge and thereby authorization of the cartridge for use with the control body.

19. The cartridge of claim 18 further comprising:

a base attached to the housing and adapted to engage a coupler of the control body to couple the cartridge with the control body to form the aerosol delivery device.

* * * * *